US009248361B1

(12) United States Patent
Jones

(10) Patent No.: US 9,248,361 B1
(45) Date of Patent: Feb. 2, 2016

(54) MOTION CAPTURE AND ANALYSIS SYSTEMS FOR USE IN TRAINING ATHLETES

(71) Applicant: Virtual Sports Training, Inc., Mission Viejo, CA (US)

(72) Inventor: Erik W. Jones, Ladera Ranch, CA (US)

(73) Assignee: Virtual Sports Training, Inc., Mission Viejo, CA (US)

( * ) Notice: Subject to any disclaimer, the term of this patent is extended or adjusted under 35 U.S.C. 154(b) by 0 days.

(21) Appl. No.: 13/747,311

(22) Filed: Jan. 22, 2013

Related U.S. Application Data

(60) Provisional application No. 61/590,523, filed on Jan. 25, 2012.

(51) Int. Cl.
*A63B 69/36* (2006.01)

(52) U.S. Cl.
CPC ...................................... *A63B 69/36* (2013.01)

(58) Field of Classification Search
USPC ...................... 348/159; 272/148 R; 340/573.1
See application file for complete search history.

(56) References Cited

U.S. PATENT DOCUMENTS

| 4,477,079 | A | 10/1984 | White |
| 5,067,717 | A | 11/1991 | Harlan et al. |
| 5,087,047 | A | 2/1992 | McConnell |
| 5,154,427 | A | 10/1992 | Harlan et al. |
| 5,282,628 | A | 2/1994 | Komori et al. |
| 5,467,992 | A | 11/1995 | Harkness |
| 5,599,239 | A | 2/1997 | Kim et al. |
| 5,634,855 | A | 6/1997 | King |
| 5,879,239 | A | 3/1999 | Macroglou |
| 5,926,780 | A | 7/1999 | Fox et al. |
| 6,261,189 | B1 | 7/2001 | Saville et al. |
| 6,371,863 | B1 | 4/2002 | Moran |
| 6,431,991 | B1 | 8/2002 | Kossnar et al. |
| 6,612,937 | B1 | 9/2003 | Whelan |
| 6,716,139 | B1 | 4/2004 | Hosseinzadeh-Dolkhani et al. |
| 6,730,047 | B2 | 5/2004 | Socci et al. |
| 6,786,730 | B2 | 9/2004 | Bleckley et al. |
| 6,939,245 | B1 | 9/2005 | Mullarkey |
| 6,959,259 | B2 * | 10/2005 | Vock et al. ..................... 702/142 |
| 7,112,145 | B2 | 9/2006 | Gaddy |
| 7,780,545 | B2 | 8/2010 | Smith et al. |
| 8,597,133 | B2 * | 12/2013 | Priester ......................... 473/257 |
| 8,626,472 | B2 * | 1/2014 | Solinsky ........................ 702/160 |
| 2003/0181832 | A1 * | 9/2003 | Carnahan et al. ............. 600/595 |
| 2003/0219704 | A1 | 11/2003 | Bleckley et al. |
| 2004/0005918 | A1 | 1/2004 | Walker et al. |
| 2005/0005874 | A1 | 1/2005 | Light et al. |
| 2005/0049113 | A1 | 3/2005 | Yueh et al. |
| 2005/0197063 | A1 | 9/2005 | White |

(Continued)

*Primary Examiner* — Masud Ahmed
(74) *Attorney, Agent, or Firm* — Stout, Uxa & Buyan, LLP; Donald E. Stout

(57) ABSTRACT

A complete closed-loop system of capture, analysis, and corrective feedback uses small unobtrusive, strategically placed sensors on the ear, hip, knee, wrist, and/or ankle that communicate wirelessly to a base unit. The sensors capture movement during an activity to be analyzed, such as a golf swing, and send data to a base unit, which processes and transmits the data to a smart phone or other suitable portable and wireless communications device. The wireless communications device, in turn, transmits the processed data to a data base in the cloud (centrally based Internet software) where software instantly analyzes the motion represented by the processed data, then provides immediate feedback for improvement to the user.

8 Claims, 5 Drawing Sheets

(56) References Cited

U.S. PATENT DOCUMENTS

| | | |
|---|---|---|
| 2005/0266961 A1 | 12/2005 | Shum et al. |
| 2005/0276570 A1 | 12/2005 | Reed et al. |
| 2006/0040757 A1 | 2/2006 | Rosselli |
| 2007/0238538 A1* | 10/2007 | Priester .................. 473/131 |
| 2007/0243942 A1 | 10/2007 | Elliot |
| 2010/0204616 A1* | 8/2010 | Shears et al. ............... 600/595 |
| 2011/0021318 A1* | 1/2011 | Lumsden et al. ............... 482/8 |
| 2011/0025853 A1* | 2/2011 | Richardson ................. 348/159 |
| 2011/0208444 A1* | 8/2011 | Solinsky ..................... 702/41 |
| 2011/0230986 A1* | 9/2011 | Lafortune et al. ............. 700/93 |
| 2012/0139731 A1* | 6/2012 | Razoumov et al. ........ 340/573.1 |

* cited by examiner

MOTION CAPTURE AND ANALYSIS SYSTEMS FOR USE IN TRAINING ATHLETES

This application claims the benefit under 35 U.S.C. 119(e) of the filing date of Provisional U.S. Application Ser. No. 61/590,523, entitled Motion Capture and Analysis Systems for Use in Training Athletes, filed on Jan. 25, 2012, which application is expressly incorporated by reference, in its entirety.

This application is also related to commonly assigned U.S. Pat. No. 7,780,545, which is also expressly incorporated herein by reference, in its entirety.

BACKGROUND OF THE INVENTION

The invention is related to motion capture, analysis, display and professional feedback for the purpose of evaluating the body motion of a subject involved in an athletic training or medical monitoring exercise.

Certain tools exist today that allow users to capture motion and analyze the motion. The tools typically comprise video-based, wearable sensor-based or wireless sensor-based approaches. Current tools have a limitation due to available equipment and the need for interpretation of gathered data. In the case of video capture, the user must have a video camera equipment setup in the location where they wish to use the equipment. In the case of wearable sensors, the sensors provide positional data that must be analyzed by a professional to provide valuable feedback to the user. None of these systems either a) are portable or b) work without a professional instructor reviewing the results and recommending correction.

SUMMARY OF THE INVENTION

The present invention solves the problems in the prior art approaches by offering a highly portable system which includes the necessary logic and analysis to provide immediate feedback and corrective instruction to the user for any suitable repetitive motion activity.

The present invention provides a complete closed loop of capture, analysis, and corrective feedback without the need to have a professional personally or manually review the results. In essence, a user has the necessary professional analysis built into the back end system to provide expert feedback to the user. Other systems rely on a professional to review captured data, or an engineer to interpret charts, graphs, and numbers.

The system uses small unobtrusive, strategically placed sensors on the ear, hip, knee, wrist, and/or ankle that communicate wirelessly to the base (ground) unit. The sensors capture the movement and send data to the base which transmits the data to a smart phone or other suitable portable and wireless communications device, which in turn transmits to a data base in the cloud (centrally based Internet software) where software instantly analyzes, evaluates, compares, or uses in competition, or uses in some application yet to be written. The possibilities for "apps" usable by the inventive system are only limited by imagination. The system is capable of handling up to eight sensors at a time, and potentially more, and can be used for serious coaching or just competitive fun in the back yard.

More particularly, there is provided a system for improving the skills of a user in a particular activity, which comprises a ground unit controller, a plurality of motion sensors for capturing the motion of a user, which are placeable at desired locations, an ear piece to be worn by the user, having a motion sensor for detecting head movement, and a transmitter for transmitting data collected by the motion sensors to a remote processor. In one embodiment, the transmitter comprises a portable wireless communications device, such as a smart phone.

The ground unit controller receives data collected by the motion sensors, and transmits the data to the smart phone. The remote processor comprises a part of the system. An instructor website application portal is provided for providing a user interface for analyzing data collected by the motion sensors and transmitted to the remote processor, and further for enabling instruction based on the aforementioned analysis.

In another aspect of the invention, there is disclosed a method of training in order to improve in the performance of a particular repeatable activity. This method comprises steps of placing a plurality of motion sensors in proximity to a user preparing to engage in a training exercise, activating a software application on a personal communications device for receiving data from the motion sensors, and transmitting the data to a remote processor. The particular activity, such as swinging a golf club, is conducted. A further step involves activating a ground unit/system controller for receiving data collected by the motion sensors and transmitting that data to the personal communications device. Still another step comprises activating an instructor website application portal having a data connection to the remote processor for viewing and evaluating the transmitted data. The data evaluation step includes comparing the data to stored data to determine appropriate corrective actions.

The invention, together with additional features and advantages thereof, may be best understood by reference to the following description taken in conjunction with the accompanying illustrative drawings. In these accompanying drawings, like reference numerals designate like parts throughout the figures.

DETAILED DESCRIPTION OF THE INVENTION

Figure 1:
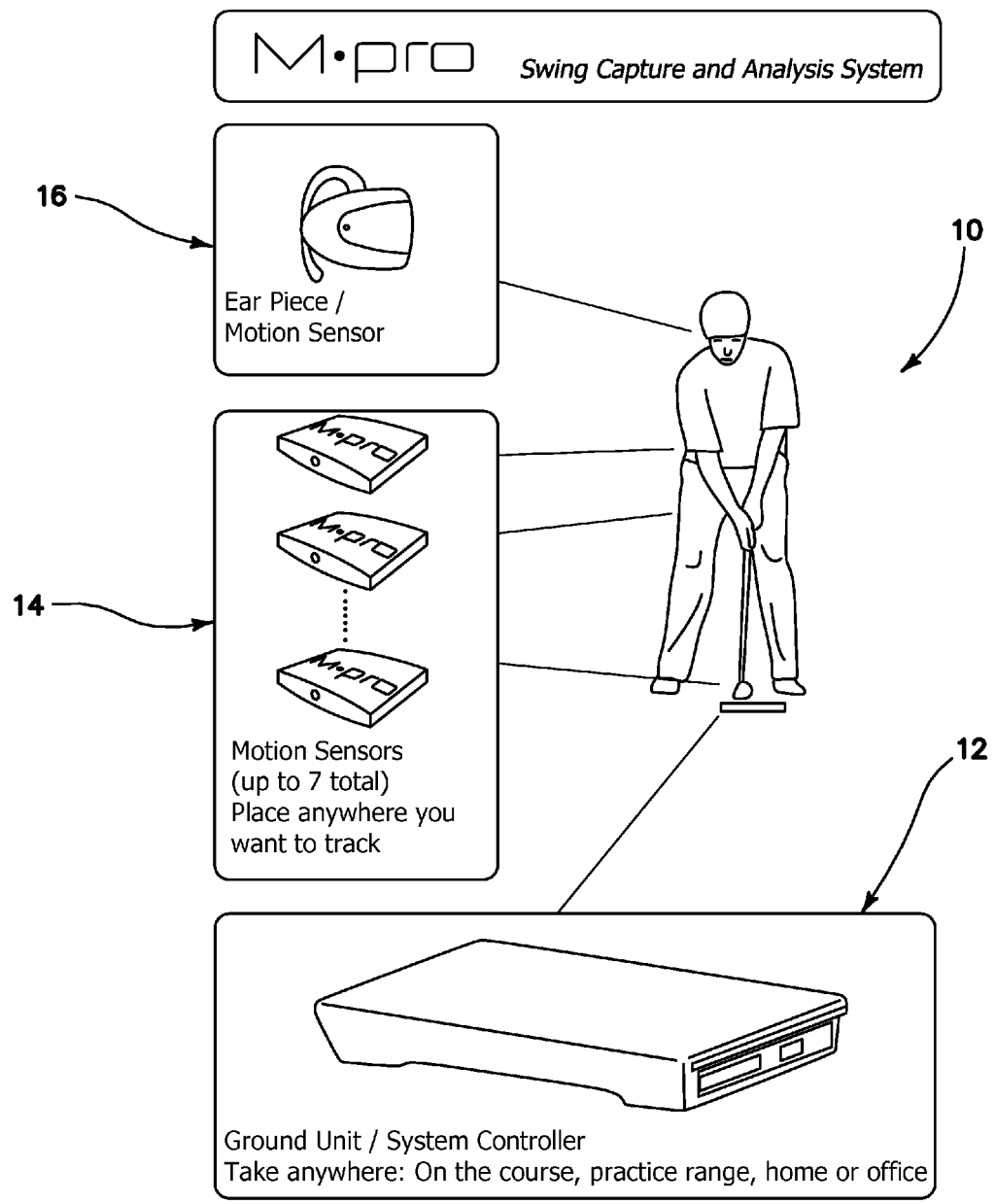
FIG. 1 is a schematic view illustrating the systemic components of the present invention.

Referring now more particularly to the drawings, a user-sited training system 10 constructed in accordance with the principles of the present invention is shown in FIG. 1. The system 10 comprises a ground unit controller 12 for storing recorded data. This unit 12 is adapted to communicate with and connect with a wireless phone or other communication device. Motion sensors 14 are provided as components of the system, and may be placed in any location suitable for capturing and recording motion of portions of the user's body or apparatus the user is manipulating, such as a golf club. As noted in the drawing, up to seven of these motion sensors are presently contemplated, depending upon application, but even more than seven could be a choice made within the scope of the present invention. An ear piece 16 is provided for capturing head motion, and aural instructional feedback.

In the illustrated example, using currently available technology, the ear piece 16 is connected to the ground unit controller 12 via Bluetooth, or the like, and the smart phone (not shown) is connected to the ground unit controller 12 by Bluetooth as well.

Figure 2:
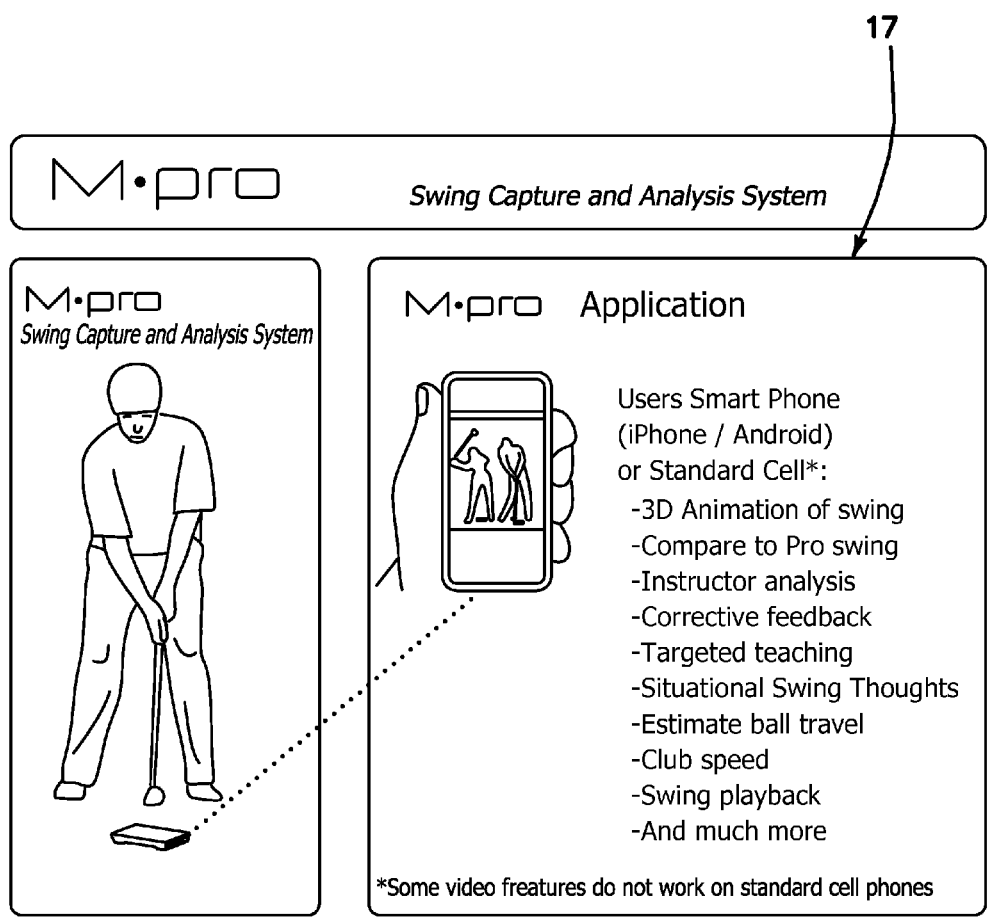
FIG. 2 is a schematic view illustrating the ground unit/system controller for the present invention.
Figure 3:
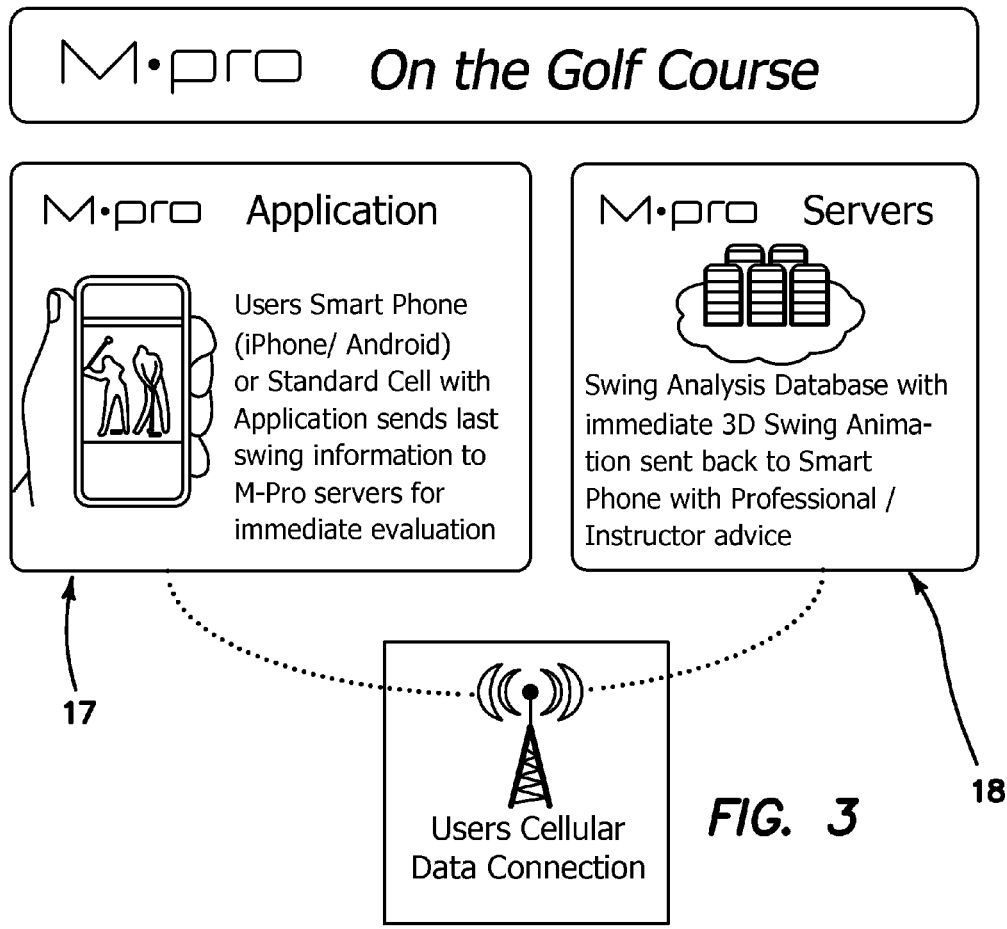
FIG. 3 is a schematic view of the communications system utilized in the inventive approach.

The advanced motion capture sensors 14 record key motions, such as the swing of a golf club from take away through swing completion. This motion capture data is wirelessly transmitted to the ground unit 12, and also may be immediately sent to the user's personal communication device, such as a smart phone, tablet computer, or the like. The phone application 17 (FIG. 2—for iPhone, Android, etc) immediately forwards the motion capture data to a powerful software application located on remote servers 18. Still using the golf swing as an example, the server software provides 3D animation of the subject's swing, further swing analysis, and audio feedback on how to correct problem areas. Sophisticated analytics immediately review the captured swing against a database of professional swings, and swing mechanics comparing known good techniques with the motion of the subject's swing. This all happens automatically right after the subject finishes his/her last swing. The system 10 is sufficiently small that it can be taken with the user while playing a round of golf, practicing at the driving range, or practicing in the office.

Figure 5:
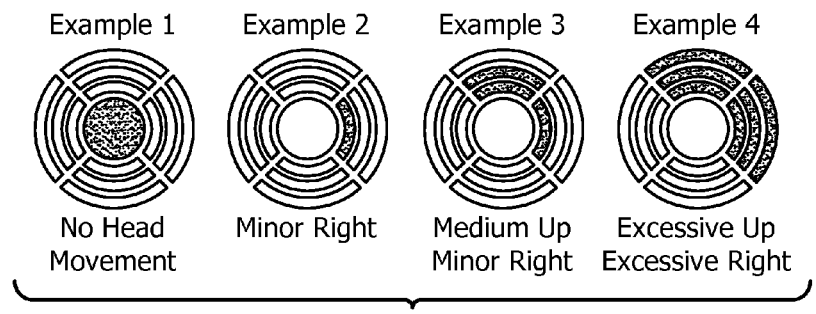
FIG. 5 is a view illustrating visual cues which might be transmitted to a user of the inventive system to provide feedback during a training exercise.
Figure 4:
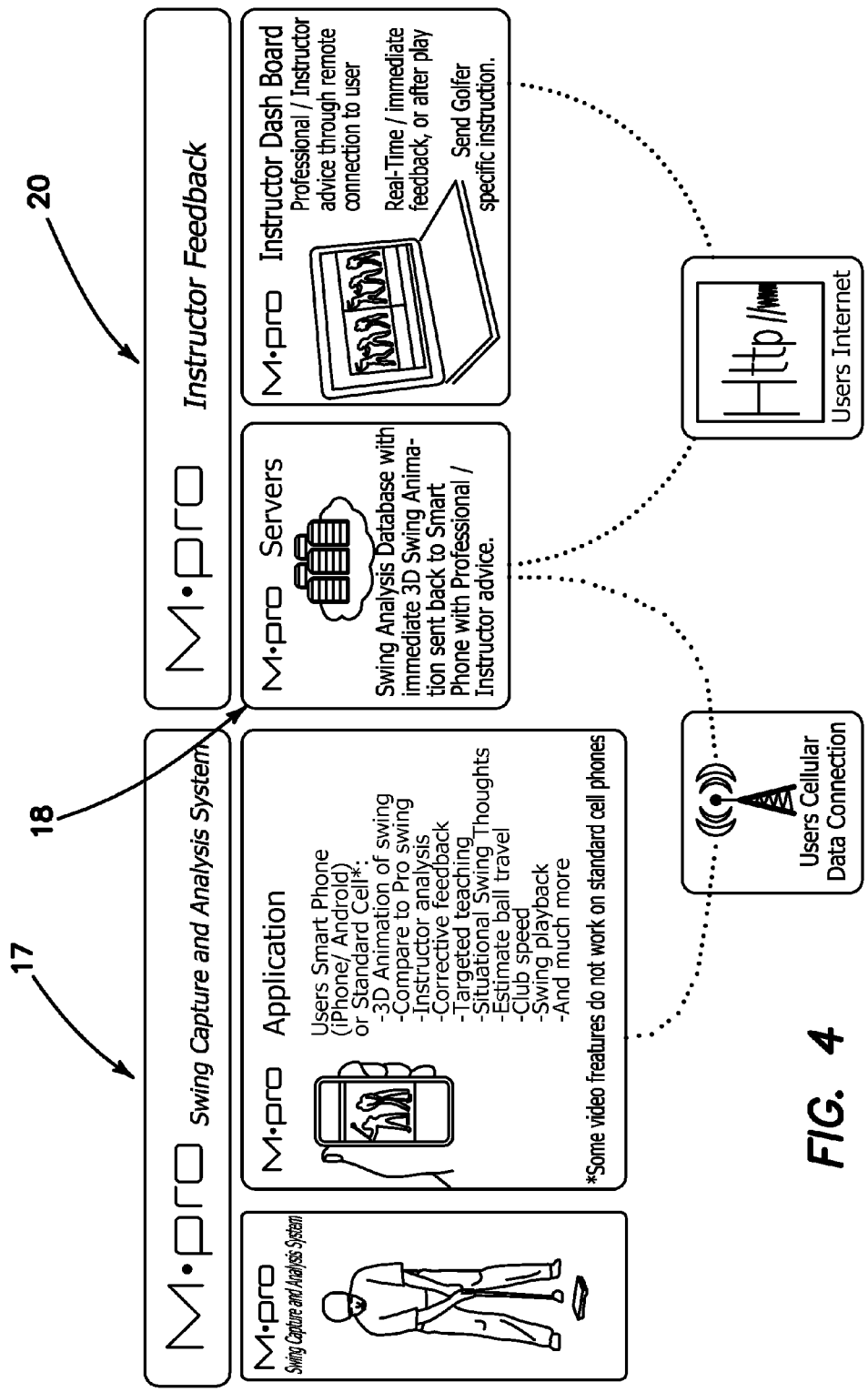
FIG. 4 is a schematic view detailing the role of communications to facilitate the inventive system's functionality.

The inventive system is an all-in-one swing analysis, professional instruction system. It can be used with a smart phone, as noted above, in practice situations to provide a 3D animation of the swing for feedback and analysis of one or multiple movements within the swing. The video can be used to compare your swing to that of various professionals, your prior swing, as stored in a database, or any other swing contained in the database. In addition, "swing thoughts", or targeted situational advice from touring professionals, are available to assist in swing improvement and mental conditioning. Since the swing analysis and evaluation are immediately available and transmitted through the user's smart phone or other suitable personal communication device, the analysis can be available to a coach or the user through an Instructor Dashboard interface 20, as shown in FIG. 4, or kept on file for future analysis and evaluation. This allows the teaching professional to optimize his time and perhaps multiply his earnings through virtual training sessions. The portal 20 thus offers ways for the coach to communicate directly and privately with his student and study the results of the analysis, and/or provides an opportunity for the student himself to research and receive additional instruction from the available database on his own FIG. 5 illustrates a series of displays which may be provided on the ground unit/system controller 12, for supplying immediate initial feedback to the subject concerning their head movement. As shown, the display is lighted and includes a gauge to indicate that the head movement is proper (no head movement for a golf swing), in which case the center of the gauge is lighted, as shown in Example 1, or minor right (Example 2—first bar to the right of center lit), or medium up, minor right (Example 3—first bar to the right and two bars above center lit), or excessive up, excessive right (Example 4). Of course, these examples are illustrative only, there are many possible combinations depending upon sensed movement.

Figure 6:
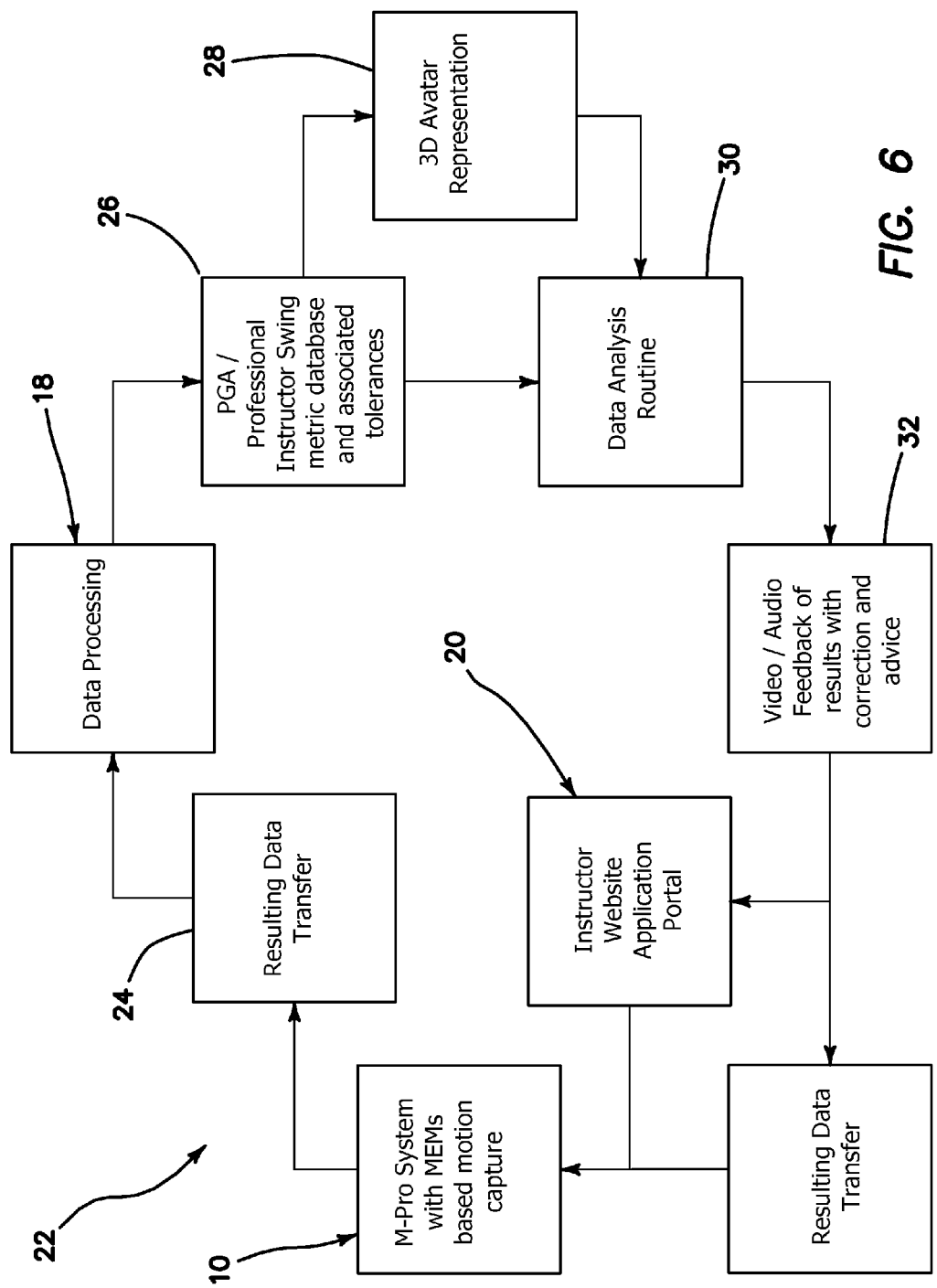
FIG. 6 is a schematic flow chart illustrating the methods of the present invention.

FIG. 6 illustrates the elements of the entire inventive training system 22, as described above, in graphical format, and how these elements might be used to process the data. As can be seen, the elements of the overall system 22 comprise the user-sited system 10, with motion capture sensors, resulting data transfer 24, data processing using the remote servers 18, a PGA/professional instructor swing metric database and associated tolerances 26, 3D Avatar representation capability 28, to provide visual feedback to the user, a data analysis routine 30, visual/audio feedback of results with correction and advice 32, and the instructor website/application portal 20.

While the aforementioned inventive systems and methods are disclosed, in presently preferred embodiments, as being related to the sport of golf, it will be appreciated by those skilled in the art that the inventive concepts taught herein are equally applicable, with suitable adaptation, to any number of other sports or other activities involving repetitive motion techniques, such as, for example, tennis, baseball, basketball, squash, skiing, and many others.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A method of training in order to improve in the performance of a particular repeatable activity, comprising:
    placing a motion sensor in a desired location;
    activating a software application on a personal communications device for receiving data from said motion sensor, and transmitting the data to a remote processor;
    conducting one repetition of a particular activity involving a repetitive motion;
    using the remote processor to process the data received from said motion sensor, compare the received data to stored data, determine proposed corrective action based on the comparison, and generate processed feedback data representing the proposed corrective action; and
    providing immediate visual feedback to a user by transmitting the processed feedback data to a display separate from the personal communications device and visible to the user while in position to conduct a next repetition, during the particular activity, regarding said proposed corrective action, so that the user may use the displayed processed feedback data to make adjustments before conducting a next repetition of the particular activity.

2. The method as recited in claim 1, and further comprising a step of activating a ground unit/system controller for receiving data collected by said motion sensor and transmitting said data to the personal communications device.

3. The method as recited in claim 1, wherein the particular activity comprises swinging a golf club.

4. The method as recited in claim 1, and further comprising activating an instructor website application portal having a data connection to said remote processor for viewing and evaluating the transmitted data.

5. The method as recited in claim 1, and further comprising a step of also providing immediate aural feedback to the user by transmitting aural suggestions regarding adjustments to be made before conducting a next repetition of the particular activity, wherein the aural feedback is received through an earpiece worn by the user while conducting the activity.

6. The method as recited in claim 1, wherein the placing step comprises placing the motion sensor on an instrument held by the user.

7. The method as recited in claim 1, wherein the placing step comprises placing a plurality of motion sensors in a plurality of desired locations.

8. The method as recited in claim 1, wherein the personal communications device comprises a smart phone.

\* \* \* \* \*